United States Patent [19]
Flomenblit et al.

[11] Patent Number: 5,882,444
[45] Date of Patent: *Mar. 16, 1999

[54] MANUFACTURE OF TWO-WAY SHAPE MEMORY DEVICES

[75] Inventors: Josef Flomenblit; Nathaly Budigina, both of Holon, Israel

[73] Assignee: Litana Ltd., Holon, Israel

[ * ] Notice: The term of this patent shall not extend beyond the expiration date of Pat. No. 5,624,508.

[21] Appl. No.: 842,213

[22] Filed: Apr. 24, 1997

Related U.S. Application Data

[63] Continuation-in-part of Ser. No. 432,802, May 2, 1995, Pat. No. 5,624,508.
[51] Int. Cl.[6] .......................... A61M 29/00; C22C 19/03
[52] U.S. Cl. ....................... 148/510; 148/511; 148/563; 623/12
[58] Field of Search .................... 148/510, 511, 148/563; 606/195, 198, 200; 623/1, 12

[56] References Cited

U.S. PATENT DOCUMENTS

| | | | |
|---|---|---|---|
| 4,753,689 | 6/1988 | Rizzo et al. | 148/563 |
| 4,919,177 | 4/1990 | Homma | 148/563 |
| 4,935,068 | 6/1990 | Duerig | 148/563 |
| 5,254,130 | 10/1993 | Poncet et al. | 606/206 |
| 5,624,508 | 4/1997 | Flomenblit et al. | 148/563 |

*Primary Examiner*—George Wyszomierski
*Attorney, Agent, or Firm*—Gary M. Nath; Harold L. Novick; Nath & Associates

[57] ABSTRACT

A process is provided for the manufacture of a two-way shape memory alloy and device. The process of the invention allows a reversible adjustment of the characteristic transformation temperatures, as well as the direction of the two-way shape memory effect, at the final stage of manufacture.

16 Claims, 1 Drawing Sheet

MANUFACTURE OF TWO-WAY SHAPE MEMORY DEVICES

This application is a Continuation-in-Part of U.S. patent application Ser. No. 08/432,802, filed May 2, 1995, the contents of which are incorporated herein in their entirety now U.S. Pat. No. 5,624,508.

FIELD OF THE INVENTION

The present invention generally relates to shape memory alloys (SMA) i.e. alloys which can switch from one shape to another, "memorized" state upon a change in temperature. More specifically, the present invention relates to an SMA which is nickel-titanium based, also known as Nitinol.

BACKGROUND OF THE INVENTION

Various metal alloys possess the ability to change their shape as a result of a change in temperature. Such SMA can undergo a reversible transformation from a martensitic state, in which the material is relatively soft and deformable, to an austenitic state in which the material possesses super elastic properties and is relatively firm. The transformation from the martensitic state to the austenitic state will be referred to herein as the "austenitic transformation", and the other transformation, from the austenitic state to the martensitic state, will be referred to herein as the "martensitic transformation". The austenitic transformation occurs over a range of temperature which is higher than the range of temperatures in which the reverse transformation occurs. This means, that once transformed to an austenitic state, an SMA will remain in that state even when cooled to a temperature below that in which the austenitic transformation began, as long as the temperature is above that in which the martensitic transformation begins.

A particular class of SMAs are alloys of nickel and titanium-NiTi alloys. NiTi alloys have found a variety of uses in medical as well as other fields. Medical uses of SMAs, particularly an NiTi-based alloy has been described in U.S. Pat. Nos. 4,665,906, 5,067,957, European Patent Application 143,580, U.S. Pat. No. 4,820,298 and many others.

For medical uses it is usually desired that the alloy will undergo an austenitic transformation over a narrow, well defined range. For example, a vascular stent of the two-way SMA type, such as that described in European Patent Application, Publication No. 625153, is typically deployed in the body while being in the martensitic state at body temperature, and then after heating, it transforms into the austenitic state, and then remains in the austenitic state when cooled to the body temperature. It can be appreciated that if excessive heating to transform the SMA from the martensitic to the austenitic state is required, this can be damaging to the surrounding tissue and is thus undesirable. Thus, it would ideally be desired that the austenitic transformation will begin at a temperature several degrees above body temperature and will be over a temperature range which will not cause tissue damage owing to the excessive heating.

GENERAL DESCRIPTION OF THE INVENTION

It is an object of the present invention to provide a process for the treatment of a NiTi-based alloy to obtain an alloy with a two-way shape memory effect (SME).

It is more specifically an object of the invention to provide such a process to obtain a two-way SME which does not require a multi-cycle "training" to yield a two-way SME.

It is still further an object of the invention to provide a process to obtain a two-way SME, with a narrow range of temperatures over which the austenitic transformation occurs.

The process of the invention has two aspects. By one aspect, to be referred to herein at times as the "said first aspect", the process yields an alloy with a direction of the austenitic and the martensitic transformations dictated by the direction of a conditioning transformation in the martensitic state. In accordance with another aspect of the invention, to be referred to herein at times as the "said second aspect", the process yields an alloy with a direction of a martensitic or austenitic transformations which is independent on the deformation introduced in the martensitic state.

In the following description and claims the term "NiTi alloy" will be used to denote an alloy comprising primarily nickel and titanium atoms but may contain also trace amounts of other metals). A NiTi alloy has typically the following empiric formula:

$$Ni_l Ti_m A_n$$

wherein A represents Na, Cu, Fe, Cr or V l, m, and n representing the proportions of the metal atoms within the alloy, the value of l, m and n being about as follows:
l=0.5
m=0.5−n
n=0.003 to 0.02.

In accordance with the invention, there is provided a process for treating a raw NiTi alloy having an initial form to obtain an alloy with a final form in which it exhibits a two-way shape memory effect (SME) whereby it has an austenitic and a martensitic memory state with associated austenitic and martensitic shapes, respectively, the process comprising the steps of:

(a) testing the raw NiTi alloy so as to obtain an estimate of the alloy's internal structure, by measuring the difference between $A_s$ and $A_f$;

(b) subjecting the raw NiTi alloy to a first heat treatment based on results obtained in (a) so as to yield alloys with an initial internal structure condition having essentially equal random dislocation density;

(c) subjecting the alloy to thermo-mechanical treatment (TMT), comprising plastic deformation of the alloy with simultaneous heating (e.g. by warm rolling or warm drawing) to yield, during dynamic ageing process (ageing while depressing), a polygonal sub-grain dislocation structure decorated by precipitation;

(d) if the deformation in step (c) did not yield the final form, subjecting the alloy to an intermediate heat treatment to conclude one cycle of sub-grain dislocation structure formation;

(e) repeating steps (c) and (d) until yielding said final form; and (f) subjecting the alloy to a final heat treatment and to a memorizing treatment.

The TMT, while it may in some instance be performed in a single step, occasionally it is necessary to do it in a few steps if the total strain value could exceed a critical value which may give rise to formation of pre-cracks (crack nucleation) in the alloy. The TMT is performed while warming the alloy typically to a temperature of about 0.3–0.6 Tm (Tm=melting temperature in °K.).

In accordance with one embodiment of the invention, the process comprising the steps of:

(a) heating a sample of the raw NiTi alloy, to a temperature of about 450°–550° C. for about 0.5–2.5 hours, and then testing the sample for temperature difference between $A_s$ and $A_f$;

(b) subjecting the raw NiTi alloy to a first heat treatment based on the $A_f$-$A_s$ difference obtained in step (a), as follows:
   where the difference is less than about 7° C., heat treating the alloy to a temperature of about 450°–500° C. for about 0.5–1.0 hours;
   where the difference is more than about 7° C., heat treating the alloy to a temperature of about 510°–550° C. for about 1.0–2.5 hours;

(c) subjecting the alloy to thermo-mechanical treatment, comprising plastic deforming the alloy at a strain rate, of less than 5 sec$^{-1}$, with simultaneous internal heating of a portion of the alloy where the deformation occurs to a temperature of about 250°–550° C., the deformation of this step being less than 55%, preferably less than 40%;

(d) if the deformation in step (c) did not yield the final form, subjecting the alloy to an intermediate heat treatment at a temperature of about 500°–550° C., for about 0.5–2 hours, and then repeating step (c); and (e) subjecting the alloy to a final heat treatment and to a memorizing treatment.

The particulars of the final heat treatment and the memorizing treatment, are different in said first aspect and in said second aspect. In accordance with said first aspect, this treatment comprises:

(i) forming the alloy into the form to be assumed by it in the austenitic state, (ii) subject the alloy to a polygonization heat treatment to yield arrangement of random dislocation, then to solution treatment to release non arranged dislocation from precipitation and provide for their rearrangement and then to an ageing treatment;

(iii) deforming the alloy to assume a conditioning form and treating it to memorize said austenitic state, which is the state into which it was formed under (i) above, and a martensitic state, in which the alloy has a martensitic form with an intermediate degree of deformation between the austenitic form and the conditioning form.

Preferably, steps (ii) and (iii) of said first aspect, comprise:

(ii) subjecting the alloy to a polygonization heat treatment at about 450°–550° C. for about 0.5–1.5 hours, then to solution treatment at about 600°–800° C. for about 2–50 mins., and then to an ageing treatment at about 350°–500° for about 0.15–2.5 hours, and (iii) deforming the alloy to assume a conditioning form, the deformation being less than about 15%, and preferably less than 7%, and being performed at a temperature T, which meets the following formula $T < M_s + 30°$ C.

wherein $M_s$ is a temperature where the martensitic transformation begins, and then heating the alloy to a temperature of or above that in which the austenitic transformation of the alloy ends.

It should be pointed out that although a single cycle of deformation in step (iii) above is usually sufficient, it may at times be desired to repeat this cycle one or more times.

In accordance with said second aspect, the final heat and memorizing treatment comprises:

(i) forming the alloy into a form other than the form to be assumed by it in the austenitic state, (ii) subjecting the alloy first to heat treatment, then to polygonization and solution treatment and then optionally to ageing treatment;

(iii) forming the alloy into a form to be assumed by it in the austenitic state, (iv) subjecting the alloy to a memorizing heat treatment and to an ageing treatment; whereby the alloy is conditioned to memorize an austenitic state in which it has an austenitic form assumed by it in (iii) above, and a martensitic state, wherein it has a martensitic form being a form with an intermediate degree of deformation between the form in which the alloy was formed in (i) above and the austenitic form.

By a preferred embodiment of said aspect, steps (ii) and (iv), comprise:

(ii) subjecting the alloy to a heat treatment at about 450°–500° C. for about 0.5–2 hours, then subjecting the alloy to polygonization and solution treatment at about 600°–800° C. for about 2–50 mins., and then subjecting the alloy to aging treatment at about 350°–500° C. for about 0–2 hours, (iv) subjecting the alloy to a memorizing heat treatment at about 500°–600° C. for more than about 10 mins., and then subjecting the alloy to ageing treatment at about 350°–500° C. for about 0.15–2.5 hours.

Following the treatment in accordance with both said first and said second embodiments, $A_f$ will be between about 10° to about 60° C. In order to increase $A_f$ and $A_s$, the alloy may then be subjected to ageing heat treatment at a temperature of about 350°–500° C. In order to decrease $A_f$ and $A_s$, the alloy can then be subjected to a solution treatment at a temperature of about 510° to about 800° C.

By differential ageing or solution treatment in different portions the alloy will have different temperatures of austenitic transformation. This is at times desired, for example, in the case of a medical stent, to have portions thereof with different transition temperatures of austenitic transformation and/or martensitic transformation.

By the above process, SMAs for a variety of applications may be prepared. Examples are medical devices, e.g. various orthopaedic devices, tooth rooth implants, medical stents, intrauterine implants, as well as non-medical devices, e.g. tube joints. A process for the preparation of such medical devices, as well as devices prepared by such process also form an aspect of the invention.

DETAILED DESCRIPTION OF THE INVENTION

Figure 1:
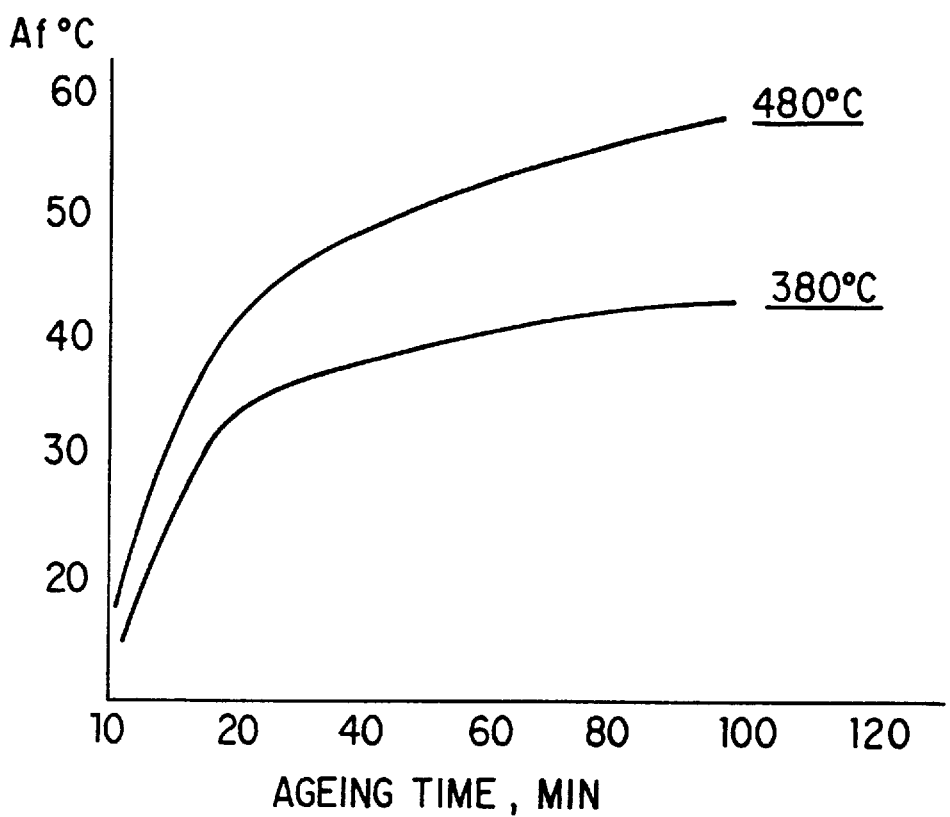
FIG. 1 in the drawings shows the relation between $A_f$ and the ageing time, in different ageing temperatures.

The temperature range over which the austenitic transformation takes place, is critical in a variety of medical applications. A specific case in point are medical stents such as those made of a two-way shape memory alloy (SMA) described in European Patent Application No. 626153. Such a shape memory (SM) device, is deployed in a tubular organ at body temperature, and then heated so as to allow the occurrence of the austenitic transformation. Once heated, it remains in the austenitic state in body temperature and supports the wall of the tubular organ. Such SM devices are designed so that the beginning of the austenitic transformation will occur at a temperature at or above 40° C. It will however be appreciated, that the range of temperature over which the austeritic transformation occurs should desirably be narrow since excessive heating where the temperature range is large, can cause tissue damage. Furthermore, a narrow temperature range will generally ensure also a more rapid transition from the martensitic to the austenitic states.

In the following description the invention will be described at times with particular reference to its application for the preparation of medical SM devices with a narrow range of austenitic transformation. It will however, be appreciated, that the invention is not limited thereto and the application of the invention to the preparation of medical stents is exemplary only. In accordance with the present invention, a raw Niti alloy, which is typically provided by manufacturers in the form of a wire or a rod is first tested for the difference between $A_s$ and $A_f$. For this purpose a small sample of the material is taken. Based on the $A_s$–$A_f$ difference, the alloy, e.g. the wire or the rod, is then subjected to a first heat treatment.

Following the first heat treatment, the alloy is subjected to a thermo-mechanical treatment (TMT) where the alloy is simultaneously heated and subjected to a mechanical deformation. In the case of a process intended for the manufacture of a medical SM device, the mechanical deformation typically involves changing the form of the alloy, from an initial form of a wire or rod, to that of a ribbon, band, etc; or alternatively, changing the wire or rod into a wire or rod of a smaller diameter. In order to retain the shape memory effect (SME) of the alloy, the total degree of deformation during the TMT, should be less than 55%, preferably less than 40%. Where the total required eventual deformation is more than 55%, the TMT is performed in two steps with an intermediate heat treatment.

The thermo-mechanical treatment may, for example, be: warm roling where the alloy is processed to be used as a medical stent; warm drawing where the alloy is processed to be used as an orthopaedic tooth root implant; etc. In warm rolling or drawing the alloy is typically heated to a temperature of about 0.3–0.6 Tm (Tm being the melting temperature in °K.). The heating of the deforming portion must be by electro-stimulation, e.g. at a current density of about 500–2000 A/cm². A big advantage of such a treatment is that in addition to causing a mechanical deformation, it leads also to heating of the pre-cracks with a high dislocation density owing to the relatively high electrical resistance at such pre-cracks which gives rise to a selective overheating at such points and heating of the pre-cracks. Moreover, clectro-stimulated warn TMT at the above current density accelerates dislocation reaction, which results in a perfect dislocation subgrain structure formation. Furthermore, the heating electrical current gives rise to a dynamic ageing process with a second phase precipitation on the walls of the subgrain dislocation cells. This structure provides for a very narrow thermal interval of austenitic transformation $A_f$–$A_s$ for the shape memory alloy, and for a variety of other advantageous properties to be explained below.

In an electrically stimulated warm rolling, where the current density decreases below 500 A/cm², or the strain rate of the deformation is above about 5 sec⁻¹, there is an increase of the random dislocation density which will decrease the degree of perfection of the subgrain structure. For a narrow $A_f$–$A_s$ intervals a subgrain structure as perfect as possible is required. Accordingly, with an increase in the random dislocation density there is an increase in the $A_f$–$A_s$ interval. For example, where the current density is about 400 A/cm², or whore strain rate is about 8 sec⁻¹, the $A_f$–$A_s$ interval after final heat treatment will be about 10°–12° C. Furthermore, increasing of the current density to above about 2000 A/cm², leads to a recrystallization process, that prevents formation of the necessary subgrain cells with precipitation on the cell walls.

The memorizing treatment involves a conditioning step in which microscopic changes within the alloy condition it to "memorize" the two forms which the alloy assumes during its use, that in the martensitic state ("martensitic form") and that in the austenitic state ("austentic form").

In accordance with said first aspect, the alloy is formed into a shape to be assumed by it in the austenitic state, e.g. in the case of a stent this involves winding on a mandrel having a diameter of a stent in the austenitic state. The alloy is then typically placed in a vacuum or inert atmosphere furnace, in which it is first subjected to a memorizing and internal structure polygonization treatment, at a temperature of about 450°–550° C. for about 0.5–1.5 hours, and then heated to about 600°–800° C. for about 2–50 mins. During this latter heating, the alloy undergoes a solution treatment with re-arrangement of dislocations which are freed after solution treatment. Subsequently, the alloy is subjected to a final aging treatment at a temperature of about 350°–500° C. for about 0.15–2.5 hours.

The result of the above treatment is a subgrain structure which imparts the alloy with several features. For one, the temperature of the austenitic transformation, $A_f$, can be adjusted within a range of 10°–60° C. with a very narrow interval of $A_f$–$A_s$ of about 1°–5° C.

In case it is desired to decrease $A_f$, the alloy may be subjected to a solution treatment at a temperature of about 510°–800° C. In order to achieve a desired $A_f$, both the temperature as well as the ageing time can be controlled. For example, where the Nitinol alloy has after the final heat treatment an $A_s$ of about 45° C. and an $A_f$ of about 48° C., after a solution treatment at 640° C. for about 5 mins., the $A_s$ and $A_f$ decrease to about 23° C. and 27° C., respectively; following solution treatment at 640° C. for 10 mins., $A_s$ and $A_f$ decrease to about 11° C. and 15° C., respectively.

In order to increase $A_f$, the alloy is subjected to an ageing heat treatment at a temperature of about 350°–500° C. Here again, in order to achieve a desired $A_f$, both the temperature as well as the ageing time can be controlled. This is demonstrated, for example, in FIG. 1 which gives the relation between the ageing time at two different temperatures (380° C. and 480° C.) and the resulting $A_f$, following a solution treatment at 640° C. for 20 mins. As can be seen, for example, ageing treatment at 380° C. for about 100 mins. yields an $A_f$ of about 40° C., with the same $A_f$ being reached with an ageing treatment at 480° C. of about 40 mins. Ageing at a temperature of about 450° C. for about 80 mins. will yield an $A_s$ of about 46° C. and an $A_f$ of about 49° C. (not shown in FIG. 1).

A unique feature of the process of the invention is the fact that the two-way SME is induced by only one cycle of deformation. In the case of said first aspect of the invention, this may be achieved by deforming the alloy into a conditioning form at a temperature of T<$M_s$+30° C. followed by heating to a temperature at or above the $A_f$ of the alloy. The deformation should be less than 15% and preferably less than 7%. A deformation above 15% will effect the internal structure of the material and yield a total or partial loss of the memory form of the austenitic state. A deformation between 7% and 15% will have only such a partial harming effect. The martensitic memory form which the alloy assumes after the above conditioning step, is an intermediate form between the austenitic memory form and the conditioning form. The direction of the two-way SME following such memorizing treatment, coincides with the direction in the martensitic state deformation. For example, where a deformation in the martensitic state involves a decrease in diameter, the diameter of the alloy in the martensitic state will be less than that of the austenitic state, and vice versa.

Generally, the process in accordance with said first aspect allows a reversible adjustment of the characteristic transformation temperatures as well as the direction of the two-way SME at the final stage of manufacture.

A final memorizing treatment in accordance with the second aspect of the invention, gives rise to a two-way SME without the need for a final deformation to induce the two-way SME. This effect is not determined when indirect SME occurs. The second aspect is useful, for example, for the manufacture of a stent with a two-way SME, and the description below will refer to this specific embodiment, The Niti ribbon or wire is wound on a mandrel having a diameter equal to $2R_1$ constrained and placed into a vacuum furnace, at a temperature of about 450°–550° C. for about 0.5–1.5 hours, so that internal structure normalization and textural formation takes place. Similarly as above, the alloy is then subjected to solution treatment and structure improvement at a temperature of 600°–800° C. for 2–50 mins. and then to an ageing treatment at 350°–500° C. for 0.15–2.5 hours. The ribbon or wire is then rewound on a mandrel with a diameter $2R_2$, which is the diameter to be assumed by the stent in the austenitic state and then subjected to a memorizing and ageing treatment at temperature of 450°–550° C. for 0.15–2 hours. If the strain of this treatment $\epsilon_{treat} = \frac{1}{2} w(1/R_2 - 1/R_1)$ <0 (w being the thickness in case of a ribbon and the diameter in case of a wire) the corresponding strain of the two-way SME during cooling $\epsilon_{tw} = \frac{1}{2} w(1/R_{tw} - 1/R_2) > 0$ ($R_{tw}$ being the diameter of the stent when assuming its martensitic state) and vice versa. As a result of this treatment, there is a very narrow temperature range in which the austenitic transformation takes place, $A_f - A_s = 1°-5°$ C., with a possibility to change $A_f$ between 10° and 60° C., similarly as above, The two-way SME in cooling may either coincide or oppose the direction of the deformation in the martensitic state. In case $R_2$ is larger than $R_1$, and $R_{tw}$ will be smaller than $R_2$, the device shrinks when it is cooled. In case $R_2$ is less than 0, i.e. a reverse bending, and $R_2$ is larger than $R_{tw}$, the device will expand when cooled.

Finally, another result of the process of the present invention is a high resistance of the formed alloy, to pitting corrosion and hydrogen embrittlement which may occur in the biological media with their relatively high chlorine ion content.

The invention will now be illustrated further by several specific examples.

EXAMPLE 1
Preparation of a Biliary Stent

The starting material was a super-elastic Niti wire, with a diameter of 1.5 mm. The Ti and Ni content of the alloy was 50 to 50.8 at % (at %=% atoms out of the total number of atoms in the alloy) and 49.1 at %, respectively. A sample of the wire was treated at a temperature of 500° C. for 1.5 hours and the temperature interval $A_f - A_s$ was determined and was found to be 15° C.

The wire was then subjected to a first heat treatment at 550° C. for two hours, and then to a thermo-mechanical electro-simulated treatment, with the current density being 900 A/cm$^2$ and the strain rate being 0.3 sec$^{-1}$. The TMT was repeated three times with two intermediate heat treatments at 500° C. for one hour each. The ribbon thickness was eventually reduced to 0.25 mm.

The ribbon was then wound and constrained on a mandrel having a diameter of 8 mm, and placed into a vacuum furnace and heated to 500° C. for 0.6 hours, and then subjected to a solution treatment at 650° C. for 30 mins. This was followed by an aging treatment at 400° C. for 1 hour.

The spiral coiled stent which was obtained had an $A_s$ of 40° C. and an $A_f$ of 43° C.

The stent was then wound on a 3 mm. diameter mandrel at a temperature of 25° C. and heated to above 43° C. for shape recovery. Thus, a stent with a two-way SME was obtained, having an austenitic memory form in which its diameter was 8 mm, a martensitic memory form to which it shrank when cooled below 25° C. in which it had a diameter of 7.3 mm.

In order to install the stent, in situ within the body, it is wound on a catheter, and then inserted into the desired place within the bile duct. The stent is then activated by raising its temperature to more than 43° C. To remove the stent it has to be cooled below 25° C. and after shrinking it can be pulled away.

EXAMPLE 2
Esophageal Stent

A stent was prepared from the same TiNi wire as used in example 1. The wire was subjected to a first heat treatment and then to a TMT, similarly as described in Example 1, the difference being that the final thickness of the wire which was obtained was 0.28 mm.

The ribbon was then wound on a mandrel having a diameter of 70 mm, was constrained and then heated to 500° C. for 1 hour and then to a solution treatment at 650° C. for 20 mins. The ribbon was then wound on a mandrel having a diameter of 16 mm., was constrained and subjected to a memorizing treatment at 520° C. for 30 mins., and then to aging treatment at 400° C. for 2 hours, The stent which was obtained after this procedure had the following parameters: $A_s = 42°$ C.; $A_f = 45°$ C.; temperature of martensitic transformation being 27° C., with the stent expanding when cooling from a diameter of 16 mm. which it had in the austeitic state to a diameter of 18 mm. in the martensitic state.

For deployment, the stent is wound on a catheter with a diameter of 5 mm, inserted into the desired place within the esophageal tract and is activated by heating above 45° C. When the stent is cooled, it expands which prevents the stent from falling into the stomach.

EXAMPLE 3
Esophageal Stent

A stent was prepared in a similar manner as that of Example 2, with the difference being that the ribbon was wound on a mandrel having a diameter of 5 mm. and after heat treatment was rewound on the mandrel with the opposite direction. After heat treatment, similarly as in Example 2, the stent expands when cooled from a diameter of 16 mm. to a diameter of 25 mm.

EXAMPLE 4
Shape Memory Force Element for Orthopedic Compression Screw

Starting material was 1.5 mm diameter NiTi wire (the composition of the alloy was 50.5 at % Ni and 49.5 at % Ti). The wire was subjected to a first heat treatment and then to a TMT, similarly as described in Example 1 (however using warm drawing instead of warm rolling).

The wire was then heat treated in straight constrained condition under a temperature of 500° C. for 0.5 hours and then subjected to a solution treatment at 650° C. for 20 mins. The wire was then released and subjected to a memorizing treatment at 520° C. for 30 mins., which was followed by an ageing treatment at 450° C. for 1 hour. After wire elongation from 20 to 21 mm, shape memory effect was obtained with $A_s=39°$ C. and $A_f=41°$ C. and after cooling up to 25° C. two way shape memory effect occurs just after heat treatment (without training) and increases after the training process (stretching-heating).

EXAMPLE 5
Shape Memory Medical Staples

Starting material and treatment was similar to that of Example 4. The final diameter which was achieved (by warm drawing) was 0.25 mm. The wire was constrained in the necessary shape and heat treated after TMT at 520° C. for 0.5 hours, solution treatment at 680° C. for 10 mins. and ageing at 450° C. for 1.5 hours.

After staple bending, shape memory effect was obtained with $A_s=42°$ C. and $A_f=45°$ C.

EXAMPLE 6
Tooth Root Implants

The starting material was a super-elastic Nitinol (50.8 at % Ni) rod with diameter of 10 mm. The rod was subjected to a first het treatment at 550° C. for 2 hours and then to a TMT—drawing at 500° C., with a strain rate of 0.5 sec$^{-1}$. The TMT was repeated 2 times with intermediate heat treatment at 500° C. for 1 hour. The rod had a final diameter of 6.0 mm.

The rod was machined into a shape of a tooth root implant with 6 force segments (legs) for anchoring into the jaw bone. The leg's length wasd 3, 4 and 5 mm for different implants. The implant was then subjected to poligonization heat treatment at 500° C., for 1 hour, then the implant's legs were distorted on the mandrel, following which the implant was subjected to heat treatment at 650° C., for 30 min and to ageing at 480° C. for 1.5 hour. Then the implant's legs were forced together with a conic cup, (from distorted diameter 5.0 mm to closed conditions with diameter 3.0 mm). While heating the implant, it causes the legs to open at temperatures: $A_s=38°$ C. and $A_f=42°$ C., that yields very gentle pressure on the jaw bone and very safe implant activation. A single cycle of straightening of the implant's legs and subsequent heating induces two way SME in the direction of joining of the legs with cooling, which feature is useful for removing the implant.

EXAMPLE 7
Two way SM tube coupling with narrow $A_s$–$A_f$ interval

A 10 mm NiTi rod identical to that which served as the starting material in Example 6 was treated in the same manner as described in Example 6 to yield a rod with a diameter of 6 mm. This rod was then machined into the shape of the hollow cylinder with an internal diameter (ID) of 4.4 mm. Then the cylinder was subjected to poligonisation and solution heat treatment: 500° C. for 1 hour and then of 680° C. for 20 min. It was then cooled, expended on a mandrel with diameter of 4.5 mm and subjected to memorising and ageing heat treatment: 530° C. for 30 min and 430° C. for 40 min. The tube coupling was then cooled and expanded on the mandrel to yield an internal diameter of 4.75 mm.

The coupling joins tubes after heating ($A_s=15°$ C., $A_f=18°$ C.) and it has two way SME in direction of reduction of ID. Thus, even with cooling it keeps pressure on the joined tubes. In comparison, conventional couplings where the two way SME is induced during installation (expansion and heating) in direction of expansion, cooling results in loosening of the coupling.

We claim:

1. A process for treating a raw NiTi alloy having an initial form to obtain an alloy with a final form in which it exhibits a two-way shape memory effect (SME) whereby it has an austenitic and a martensitic memory state with associated austenitic and martensitic shapes, respectively, the process comprising the steps of:

(a) testing the raw NiTi-based alloy so as to obtain an estimate of the alloy's internal structure, by measuring the difference between $A_s$ and $A_f$, wherein $A_s$ is a temperature where austenitic transformation, namely transformation between the martensitic to the austenitic state, begins, and $A_f$ is a temperature where the austenitic transformation ends;

(b) subjecting the raw NiTi alloy to a first heat treatment at a temperature and for a time determined on the basis of the $A_f$-$A_s$ difference obtained in step (a) so as to yield alloys with an initial internal structure condition having essentially equal random dislocation density;

(c) subjecting the alloy to thermo-mechanical treatment (TMT), comprising plastic deformation of the alloy with simultaneous heating during a dynamic ageing process, to yield a polygonal sub-grain dislocation structure containing precipitates;

(d) if the deformation in step (c) did not yield the final form, subjecting the alloy to an intermediate heat treatment to conclude one cycle of sub-grain dislocation structure formation;

(e) repeating steps (c) and (d) until yielding said final form; and (f) subjecting the alloy to a final heat treatment and to a memorizing treatment.

2. A process according to claim 1, comprising the steps of:

(a) heating a sample of the raw NiTi alloy, at a temperature of about 450°–550° C. for about 0.5–2.5 hours, and then testing the sample for temperature difference between $A_s$ and $A_f$;

(b) subjecting the raw NiTi alloy to a first heat treatment based on the $A_f$-$A_s$ difference obtained in step (a), as follows:

where the difference is less than about 7° C., heat treating the alloy at a temperature of about 450°–500° C. for about 0.5–1.0 hours;

where the difference is more than about 7° C., heat treating the alloy at a temperature of about 510°–550° C. for about 1.0–2.5 hours;

(c) subjecting the alloy to TMT, comprising plastic deforming the alloy at a strain rate, of less than 5 sec$^{-1}$, with simultaneous internal heating of a portion of the alloy where the deformation occurs at a temperature of about 250°–550° C., the deformation of this step being less than 55%;

(d) if the deformation in step (c) did not yield the final form, subjecting the alloy to an intermediate heat treatment at a temperature of about 500°–550° C., for about 0.5–2 hours, and then repeating step (c); and (e) subjecting the alloy to a final heat treatment and to a memorizing treatment.

3. A process according to claim 2, wherein the deformation in step (c) is less than 40%.

4. A process according to claim 1, wherein the final heat and memorizing treatment comprises:

(i) forming the alloy into the form to be assumed by it in the austenitic state, (ii) subject the alloy to a polygonization heat treatment to yield arrangement of random dislocation, then to solution treatment to release non arranged dislocation from precipitation and provide for their rearrangement and then to an ageing treatment;

(iii) deforming the alloy to assume a conditioning form and treating it to memorize said austenitic state, which is the state into which it was formed under (i) above, and a martensitic state, in which the alloy has a martensitic form with an intermediate degree of deformation between the austenitic form and the conditioning form.

5. A process according to claim 4, wherein the final heat and memorizing treatment comprises:

(i) forming the alloy into the form to be assumed by it in the austenitic state;

(ii) subjecting the alloy to a polygonization heat treatment at about 450°–550° C. for about 0.5–1.5 hours, then to solution treatment at about 600°–800° C. for about 2–50 mins., and then to an aging treatment at about 350°–500° C. for about 0.15–2.5 hours, and (iii) deforming the alloy to assume a conditioning form, the deformation being less than about 15%, and being performed at a temperature T, which meets the following formula $$T < M_s + 30° \text{ C.}$$

wherein $M_s$, is a temperature where the martensitic transformation begins, and then heating the alloy to a temperature of or above that in which the austenitic transformation of the alloy ends.

6. A process according to claim 5, wherein the deformation of the alloy to assume the conditioning form in step (e) (iii), is less than about 7%.

7. A process according to claim 5, comprising:

(a) adjusting the temperature in which the austenitic transformation occurs, by either an aging treatment at a temperature of about 350°–500° C., to increase the temperature in which the austenitic transformation occurs, or a solution treatment at a temperature of about 510°–800° C., to decrease the temperature in which the austenitic transformation occurs.

8. A process according to claim 5, wherein the simultaneous internal heating in step (c) comprises electro-stimulation with a current density of about 500–2000 A/cm².

9. A process according to claim 1, wherein the final heat and memorizing treatment comprises:

(i) forming the alloy into a form other than the form to be assumed by it in the austenitic state, (ii) subjecting the alloy first to heat treatment, then to polygonization and solution treatment and then optionally to ageing treatment;

(iii) forming the alloy into a form to be assumed by it in the austenitic state, (iv) subjecting the alloy to a memorizing heat treatment and to an ageing treatment;

whereby the alloy is conditioned to memorize an austenitic state in which it has an austenitic form assumed by it in (iii) above, and a martensitic state, wherein it has a martensitic form being a form with an intermediate degree of deformation between the form in which the alloy was formed in (i) above and the austenitic form.

10. A process according to claim 9, wherein the final heat and memorizing treatment comprises:

(i) forming the alloy into a form other than the form to be assumed by it in the austenitic state, (ii) subjecting the alloy to a heat treatment at about 450°–500° C. for about 0.5–2 hours, then subjecting the alloy to polygonization and solution treatment at about 600°–800° C. for about 2–50 mins., and then subjecting the alloy to aging treatment at about 350°–500° C. for about 0–2 hours, (iii) forming the alloy into a form to be assumed by it in the austenitic state, and (iv) subjecting the alloy to a memorizing heat treatment at about 500°–600° C. for more than about 10 mins., and then subjecting the alloy to aging treatment at about 350°–500° C. for about 0.15–2.5 hours.

11. A process for preparing a medical device comprising a shape memory alloy (SMA) embodying a two-way shape memory effect, comprising treating the SMA in accordance with the process defined in claim 1.

12. A process according to claim 11, wherein said medical device is a stent.

13. A process for the manufacture of a medical stent from a NiTi alloy, being a wire having a first diameter, the stent having either the form of a wire with a second diameter or a form of a band, the stent exhibiting a two-way shape memory effect (SME) having an austenitic and a martensitic memory state with associated austenitic and martensitic shapes, respectively, the process comprising the steps of:

(a) heating a sample of the NiTi wire at a temperature of about 450°–550° C. for about 0.5–2.5 hours, and then testing the sample for temperature difference between $A_s$ and $A_f$, where $A_s$ is a temperature wherein austenitic transformation, namely transformation between the martensitic to the austenitic state, begins, and $A_f$ is a temperature where the austenitic transformation ends;

(b) subjecting the wire to a first heat treatment based on the $A_f$-$A_s$ difference obtained in step (a), as follows:

where the difference is less than about 7° C., heat treating the wire at a temperature of about 450°–500° C. for about 0.5–1.0 hours;

where the difference is more than about 7° C., heat treating the wire at a temperature of about 510°–550° C. for about 1.0–2.5 hours;

(c) subjecting the wire to a thermo-mechanical treatment, comprising warm rolling of the wire at a strain rate of less than 5 sec⁻¹, with simultaneous internal heating of a portion of the wire where the deformation occurs, the heating by electro-stimulation at a current density of about 500–2000 A/cm², the deformation in this step being less than 55%;

(d) where the deformation in step (c) did not yield a cross-sectional shape of the final form, subjecting wire to an intermediate heat treatment at a temperature of about 500°–550° C., for about 0.5–2 hours and then repeating step (c); and (e) subjecting the wire to a final heat treatment and to a memorizing treatment, which comprises:

(i) winding the wire or band obtained in step (c) on a mandrel having a diameter to be assumed by the stent in the austenitic state, (ii) subjecting the wire to a polygonization heat treatment at about 450°–550° C. for about 0.5–1.5 hours, then to solution treatment at about 600°–800° C. for about 2–50 mins., and then to an aging treatment at about 350°–500° C. for about 0.15–205 hours, (iii) deforming the wire by winding it on a mandrel having a conditioning diameter, the deformation being less than about 7%, and being performed at a temperature T, which meets the following formula $T < M_s + 30°$ C.

wherein $M_s$ is a temperature where the martensitic transformation begins, and then heating the wire or band to a temperature at or above that in which the austenitic transformation ends;

whereby a stent is obtained with an austenitic state in which it has a diameter assumed in (i) above and a martensitic state in which it has a diameter which is an intermediate diameter between the conditioning diameter and the austenitic diameter.

14. A process for the manufacture of a medical stent from a wire made of a NiTi alloy having a first diameter, the stent having either the form of a wire with a second diameter or a form of a band, the stent exhibiting a two-way shape memory effect (SME) having an austenitic and a martensitic memory state with associated austenitic and martensitic shapes, respectively, the process comprising the steps of:

(a) heating a sample of the wire at a temperature of about 450°–550° C. for about 0.5–2.5 hours, and then testing the sample for temperature difference between $A_s$ and $A_f$ wherein $A_s$, is a temperature wherein austenitic transformation, namely transformation between the martensitic to the austenitic state, begins, and $A_f$ is a temperature where the austenitic transformation ends;

(b) subjecting the wire to a first heat treatment based on the $A_f$-$A_s$ difference obtained in step (a), as follows:
where the difference is less than about 7° C., heat treating the wire at a temperature of about 450°–500C. for about 0.5–1.0 hours;
where the difference is more than about 7° C., heat treating the wire at a temperature of about 510°–550° C. for about 1.0–2.5 hours;

(c) subjecting the wire to a thermo-mechanical treatment, comprising warm roiling of the wire at a strain rate of less than 5 sec$^{-1}$, with simultaneous internal heating of a portion of the wire where the deformation occurs, by electro-stimulation at a current density of about 500–2000 A/cm$^2$, the deformation in this step being less than 55%;

(d) where the deformation in step (c) did not yield a cross-sectional shape of the final form, subjecting wire to an intermediate heat treatment at a temperature of about 500°–550° C., for about 0–2 hours and then repeating step (c); and (e) subjecting the wire to a final heat treatment and to a memorizing treatment, which comprises:
(i) winding the wire or band obtained in step (c) on a mandrel having a conditioning diameter being different than the diameter to be assumed by the stent in the austenitic state,
(ii) subjecting the wire to a heat treatment at about 450°–500° C. for about 0.5–2 hours, then to polygonization and solution treatment about 600°–800° C. for about 2–50 mins., and then to aging treatment at about 350°–300° C. for about 0–2 hours,
(iii) winding the wire or band on a mandrel having a diameter to be assumed by the stent in the austenitic state,
(iv) subjecting the alloy to a memorizing heat treatment at about 500°–600° C. for more than about 10 mins., and then to aging treatment at about 350°–500° C. for about 0.15–2.15 hours;

whereby a stent is obtained having an austenitic state with a diameter into which the wire was formed in step (iii), and a martensitic state in which the stent has a diameter which is an intermediate diameter between the conditioning diameter and the diameter of the stent in the austenitic state.

15. A process for the manufacture of tooth root implant from a NiTi alloy, exhibiting a two way SME having an austenitic and a martensitic memory state with associated austenitic and martensitic shapes, respectively, the process comprising the steps of:

(a) heating a sample of a NiTi rod at a temperature of about 450°–550° C. for about 0.5–2.5 hours, and then testing the sample for temperature difference between $A_s$ and $A_f$, wherein $A_s$ is a temperature wherein austenitic transformation, namely transformation between the martensitic to the austenitic state, begins, and $A_f$ is a temperature where the austenitic transformation ends;

(b) subjecting the rod to a first heat treatment based on the $A_f$-$A_s$ difference obtained in step (a), as follows:
where the difference is less than about 7° C., heat treating the wire at a temperature of about 450°–500° C. for about 0.5–1.0 hours;
where the difference is more than about 7° C., heat treating the wire at a temperature of about 510°–550° C. for about 1.0–2.5 hours (c) subjecting the rod to a TMT comprising warm drawing with a strain rate less than 5 sec$^{-1}$ with simultaneous heating, the total strain in this step being less than 55%;

(d) where the deformation in step (c) did not yield a cross-sectional shape of the final form, subjecting the rod to an intermediate heat treatment at a temperature of about 500°–550° C., for about 0.5–2 hours and then repeating step (c);

(e) machining the rod to yield the shape of the implant;

(f) subjecting the implant to the final heat treatment and to a memorizing treatment, which comprises:
(i) expanding implant's force segments to a diameter to be assumed by the implant in the austenitic state,
(ii) subjecting the implant to a polygonization heat treatment at about 450°–550° C. for about 0.5–1.5 hours, then to solution treatment at about 600°–800° C. for about 2–50 min, and then to an ageing treatment at about 350°–500° C. for about 0.15–2.5 hours,
(iii) deforming the implant force segments to a conditioning diameter with a strain less than about 7% and being performed at temperature $T<M_s+30°$ C., wherein $M_s$ is a temperature where the martensitic transformation begins and then heating the implant to a temperature at or above that in which the austenitic transformation ends;

whereby an implant is obtained with an austenitic state in which it has a diameter assumed in (i) above and a martensitic state in which it has a diameter, which is an intermediate diameter between the conditioning diameter and the austenitic diameter.

16. A process for the manufacture of tube coupling from a NiTi alloy, exhibiting a two way SME having an austenitic and a martensitic memory state with associated austenitic and martensitic shapes, respectively, the process comprising the steps of:

(a) heating a sample of a NiTi rod at a temperature of about 450°–550° C. for about 0.5–2.5 hours, and then testing the sample for temperature difference between $A_s$ and $A_f$ wherein $A_s$, is a temperature wherein austenitic transformation, namely transformation between the martensitic to the austenitic state, begins, and $A_f$ is a temperature where the austenitic transformation ends;

(b) subjecting the rod to a first heat treatment based on the $A_f$-$A_s$, difference obtained in step (a), as follows:
where the difference is less than about 7° C., heat treating the wire at a temperature of about 450°–500° C. for about 0.5–1.0 hours;
where the difference is more than about 7° C., heat treating the wire at a temperature of about 510°–550° C. for about 1.0–2.5 hours;

(c) subjecting the rod to a TMT comprising warm drawing with a strain rate less than 5 sec$^{-1}$ with simultaneous heating, the total strain in this step being less than 55%;

(d) where the deformation in step (c) did not yield a cross-sectional shape of the final form, subjecting the rod to an intermediate heat treatment at a temperature of about 500°–550° C., for about 0.5–2 hours and then repeating step (c); and (e) machining the rod to yield the shape of the implant;

(f) subjecting the implant to the final heat treatment and to a memorizing treatment, which comprises:
  (i) subjecting the coupling to a polygonization heat treatment at about 450°–550° C. for about 0.5–1.5 hours, then to solution treatment at about 600°–800° C. for about 2–50 min and then to an ageing treatment at about 350°–500° C. for about 0–2.5 hours,
  (ii) expanding the coupling to a diameter to be assumed by the coupling in the austenitic state,
  (iii) subjecting the coupling to a memorizing heat treatment at about 500°–600° C. for more than about 10 mins, and then to an ageing treatment at about 350°–500° C. for about 0.15–2.5 hours, whereby a coupling is obtained having an austenitic state with a diameter into which it was formed in step (ii) and a martensitic state in which the coupling has a diameter which is intermediate diameter between the conditioning ID and the diameter of the coupling in the austenitic state.

* * * * *